United States Patent
Patel (10) Patent No.: US 12,208,004 B2
(45) Date of Patent: *Jan. 28, 2025

(54) IMPLANT DELIVERY CAPSULE

(71) Applicant: Edwards Lifesciences Corporation, Irvine, CA (US)

(72) Inventor: Darshin S. Patel, San Juan Capistrano, CA (US)

(73) Assignee: EDWARDS LIFESCIENCES CORPORATION, Irvine, CA (US)

(*) Notice: Subject to any disclaimer, the term of this patent is extended or adjusted under 35 U.S.C. 154(b) by 210 days.

This patent is subject to a terminal disclaimer.

(21) Appl. No.: 17/875,993

(22) Filed: Jul. 28, 2022

(65) Prior Publication Data

US 2022/0362018 A1 Nov. 17, 2022

Related U.S. Application Data

(63) Continuation of application No. 16/448,418, filed on Jun. 21, 2019, now Pat. No. 11,399,937, which is a continuation of application No. 15/331,564, filed on Oct. 21, 2016, now Pat. No. 10,350,067.

(60) Provisional application No. 62/246,510, filed on Oct. 26, 2015.

(51) Int. Cl.
*A61F 2/24* (2006.01)
*A61F 2/966* (2013.01)
*A61M 25/06* (2006.01)

(52) U.S. Cl.
CPC .......... *A61F 2/2436* (2013.01); *A61F 2/2427* (2013.01); *A61F 2/966* (2013.01); *A61F 2230/005* (2013.01); *A61F 2230/0069* (2013.01); *A61M 2025/0681* (2013.01)

(58) Field of Classification Search
CPC ....... A61F 2/2436; A61F 2/2427; A61F 2/966
See application file for complete search history.

(56) References Cited

U.S. PATENT DOCUMENTS

| | | |
|---|---|---|
| 519,297 A | 5/1894 | Bauer |
| 4,035,849 A | 7/1977 | Angell et al. |
| 4,592,340 A | 6/1986 | Boyles |
| 4,955,895 A | 9/1990 | Sugiyama et al. |
| 4,994,077 A | 2/1991 | Dobben |
| 5,059,177 A | 10/1991 | Towne et al. |
| 5,176,698 A | 1/1993 | Burns et al. |
| 5,192,297 A | 3/1993 | Hull |

(Continued)

FOREIGN PATENT DOCUMENTS

| | | |
|---|---|---|
| DE | 19532846 A1 | 3/1997 |
| DE | 19907646 A1 | 8/2000 |

(Continued)

*Primary Examiner* — Phong Son H Dang
(74) *Attorney, Agent, or Firm* — Meunier Carlin Curfman LLC; Sean Seung Kyu Kim (57) ABSTRACT

A delivery system for delivering a stent-mounted heart valve, or other implant, through an introducer sheath. The delivery system includes an elongate catheter supporting a capsule. The capsule contains the stent-mounted heart valve in the crimped condition. The capsule includes a protrusion extending from its outer surface for urging the sheath away from the outer surface capsule as it moves therethrough, thereby reducing an average peak push force resulting from advancement of the capsule through the sheath.

20 Claims, 9 Drawing Sheets

(56) References Cited

U.S. PATENT DOCUMENTS

| | | | |
|---|---|---|---|
| 5,266,073 A | 11/1993 | Wall | |
| 5,325,845 A | 7/1994 | Adair | |
| 5,358,496 A | 10/1994 | Ortiz et al. | |
| 5,395,349 A * | 3/1995 | Quiachon | A61B 17/3462 |
| | | | 604/167.03 |
| 5,411,552 A | 5/1995 | Andersen et al. | |
| 5,554,185 A | 9/1996 | Block et al. | |
| 5,591,195 A | 1/1997 | Taheri et al. | |
| 5,599,305 A | 2/1997 | Hermann et al. | |
| 5,632,760 A | 5/1997 | Sheiban et al. | |
| 5,639,274 A | 6/1997 | Fischell et al. | |
| 5,728,068 A | 3/1998 | Leone et al. | |
| 5,749,890 A | 5/1998 | Shaknovich | |
| 5,782,809 A | 7/1998 | Umeno et al. | |
| 5,824,044 A | 10/1998 | Quiachon et al. | |
| 5,840,081 A | 11/1998 | Andersen et al. | |
| 5,908,405 A | 6/1999 | Imran et al. | |
| 5,916,147 A | 6/1999 | Boury | |
| 5,944,690 A | 8/1999 | Falwell et al. | |
| 5,961,536 A | 10/1999 | Mickley et al. | |
| 5,968,068 A | 10/1999 | Dehdashtian et al. | |
| 6,019,777 A | 2/2000 | Mackenzie | |
| 6,027,510 A | 2/2000 | Alt | |
| 6,033,381 A | 3/2000 | Kontos | |
| 6,143,016 A | 11/2000 | Bleam et al. | |
| 6,162,208 A | 12/2000 | Hipps | |
| 6,168,614 B1 | 1/2001 | Andersen et al. | |
| 6,174,327 B1 | 1/2001 | Mertens et al. | |
| 6,217,585 B1 | 4/2001 | Houser et al. | |
| 6,235,050 B1 | 5/2001 | Quiachon et al. | |
| 6,251,092 B1 | 6/2001 | Qin et al. | |
| 6,379,372 B1 | 4/2002 | Dehdashtian et al. | |
| 6,383,171 B1 | 5/2002 | Gifford et al. | |
| 6,454,799 B1 | 9/2002 | Schreck | |
| 6,458,153 B1 | 10/2002 | Bailey et al. | |
| 6,461,382 B1 | 10/2002 | Cao | |
| 6,471,672 B1 | 10/2002 | Brown et al. | |
| 6,500,147 B2 | 12/2002 | Omaleki et al. | |
| 6,508,790 B1 * | 1/2003 | Lawrence | A61M 1/3661 |
| | | | 604/167.05 |
| 6,514,228 B1 | 2/2003 | Hamilton et al. | |
| 6,527,979 B2 | 3/2003 | Constantz et al. | |
| 6,579,305 B1 | 6/2003 | Lashinski | |
| 6,582,462 B1 | 6/2003 | Andersen et al. | |
| 6,652,492 B1 * | 11/2003 | Bell | A61M 25/0075 |
| | | | 604/537 |
| 6,652,578 B2 | 11/2003 | Bailey et al. | |
| 6,730,118 B2 | 5/2004 | Spenser et al. | |
| 6,733,525 B2 | 5/2004 | Yang et al. | |
| 6,764,504 B2 | 7/2004 | Wang et al. | |
| 6,767,362 B2 | 7/2004 | Schreck | |
| 6,808,520 B1 * | 10/2004 | Fourkas | A61M 39/0613 |
| | | | 604/524 |
| 6,830,584 B1 | 12/2004 | Seguin | |
| 6,893,460 B2 | 5/2005 | Spenser et al. | |
| 6,908,481 B2 | 6/2005 | Cribier | |
| 7,011,094 B2 | 3/2006 | Rapacki et al. | |
| 7,018,406 B2 | 3/2006 | Seguin et al. | |
| 7,018,408 B2 | 3/2006 | Bailey et al. | |
| 7,137,993 B2 | 11/2006 | Acosta et al. | |
| 7,182,779 B2 * | 2/2007 | Acosta | A61F 2/915 |
| | | | 623/1.11 |
| 7,276,084 B2 | 10/2007 | Yang et al. | |
| 7,318,278 B2 | 1/2008 | Zhang et al. | |
| 7,320,702 B2 * | 1/2008 | Hammersmark | A61F 2/915 |
| | | | 623/1.11 |
| 7,320,704 B2 | 1/2008 | Lashinski et al. | |
| 7,374,571 B2 | 5/2008 | Pease et al. | |
| 7,393,360 B2 | 7/2008 | Spenser et al. | |
| 7,435,257 B2 | 10/2008 | Lashinski et al. | |
| 7,510,575 B2 | 3/2009 | Spenser et al. | |
| 7,585,321 B2 | 9/2009 | Cribier | |
| 7,594,926 B2 | 9/2009 | Linder et al. | |
| 7,597,709 B2 | 10/2009 | Goodin | |
| 7,618,446 B2 | 11/2009 | Andersen et al. | |
| 7,780,723 B2 | 8/2010 | Taylor | |
| 7,785,366 B2 | 8/2010 | Maurer et al. | |
| 7,892,273 B2 * | 2/2011 | George | A61F 2/958 |
| | | | 623/1.11 |
| 7,959,661 B2 * | 6/2011 | Hijlkema | A61F 2/95 |
| | | | 623/1.12 |
| 8,029,556 B2 | 10/2011 | Rowe | |
| 8,167,932 B2 | 5/2012 | Bourang et al. | |
| 8,172,891 B2 | 5/2012 | Shelso | |
| 8,313,525 B2 * | 11/2012 | Tuval | A61F 2/2427 |
| | | | 623/2.11 |
| RE43,882 E | 12/2012 | Hopkins et al. | |
| 8,449,606 B2 | 5/2013 | Eliasen et al. | |
| 8,475,523 B2 | 7/2013 | Duffy | |
| 8,486,132 B2 * | 7/2013 | Snow | A61F 2/915 |
| | | | 623/1.11 |
| 8,512,398 B2 * | 8/2013 | Alkhatib | A61F 2/013 |
| | | | 623/2.11 |
| 8,568,472 B2 | 10/2013 | Marchand et al. | |
| 8,623,075 B2 * | 1/2014 | Murray, III | A61F 2/2439 |
| | | | 623/2.11 |
| 8,652,198 B2 * | 2/2014 | Andreas | A61F 2/91 |
| | | | 623/1.11 |
| 8,747,459 B2 * | 6/2014 | Nguyen | A61F 2/2436 |
| | | | 623/2.11 |
| 8,790,387 B2 * | 7/2014 | Nguyen | A61F 2/2433 |
| | | | 604/525 |
| 8,876,878 B2 * | 11/2014 | Dwork | A61F 2/95 |
| | | | 606/108 |
| 9,061,119 B2 | 6/2015 | Le et al. | |
| 9,119,716 B2 | 9/2015 | Lee et al. | |
| 9,277,993 B2 * | 3/2016 | Gamarra | A61F 2/2436 |
| 9,561,102 B2 * | 2/2017 | Rust | A61F 2/2436 |
| 9,795,477 B2 | 10/2017 | Tran et al. | |
| 10,004,599 B2 * | 6/2018 | Rabito | A61F 2/2439 |
| 11,273,038 B2 | 3/2022 | Tang et al. | |
| 2001/0002445 A1 | 5/2001 | Vesely | |
| 2001/0007082 A1 | 7/2001 | Dusbabek et al. | |
| 2002/0032481 A1 | 3/2002 | Gabbay | |
| 2002/0058995 A1 | 5/2002 | Stevens | |
| 2002/0165461 A1 | 11/2002 | Hayzelden et al. | |
| 2003/0040792 A1 | 2/2003 | Gabbay | |
| 2003/0050694 A1 | 3/2003 | Yang et al. | |
| 2003/0120341 A1 | 6/2003 | Shennib et al. | |
| 2004/0093061 A1 | 5/2004 | Acosta et al. | |
| 2004/0093063 A1 * | 5/2004 | Wright | A61F 2/95 |
| | | | 623/1.12 |
| 2004/0133263 A1 | 7/2004 | Dusbabek et al. | |
| 2004/0143197 A1 | 7/2004 | Soukup et al. | |
| 2004/0148007 A1 | 7/2004 | Jackson et al. | |
| 2004/0186563 A1 | 9/2004 | Lobbi | |
| 2004/0186565 A1 | 9/2004 | Schreck | |
| 2004/0260389 A1 | 12/2004 | Case et al. | |
| 2005/0080474 A1 * | 4/2005 | Andreas | A61F 2/958 |
| | | | 623/1.11 |
| 2005/0096736 A1 | 5/2005 | Osse et al. | |
| 2005/0137689 A1 | 6/2005 | Salahieh et al. | |
| 2005/0149160 A1 | 7/2005 | McFerran | |
| 2005/0203614 A1 | 9/2005 | Forster et al. | |
| 2005/0203617 A1 | 9/2005 | Forster et al. | |
| 2005/0245894 A1 | 11/2005 | Zadno-Azizi | |
| 2005/0288763 A1 | 12/2005 | Andreas et al. | |
| 2005/0288766 A1 * | 12/2005 | Plain | A61F 2/97 |
| | | | 623/1.12 |
| 2006/0025857 A1 | 2/2006 | Bergheim et al. | |
| 2006/0052750 A1 * | 3/2006 | Lenker | A61B 17/3439 |
| | | | 604/164.01 |
| 2006/0184226 A1 * | 8/2006 | Austin | A61F 2/95 |
| | | | 623/1.11 |
| 2006/0282150 A1 | 12/2006 | Olson et al. | |
| 2007/0005131 A1 | 1/2007 | Taylor | |
| 2007/0073389 A1 | 3/2007 | Bolduc et al. | |
| 2007/0088431 A1 | 4/2007 | Bourang et al. | |
| 2007/0100356 A1 | 5/2007 | Lucatero et al. | |
| 2007/0112422 A1 | 5/2007 | Dehdashtian | |
| 2007/0203575 A1 | 8/2007 | Forster et al. | |
| 2007/0219612 A1 | 9/2007 | Andreas et al. | |

(56) References Cited

U.S. PATENT DOCUMENTS

| | | |
|---|---|---|
| 2007/0239254 A1 | 10/2007 | Chia et al. |
| 2007/0244546 A1 | 10/2007 | Francis |
| 2007/0265700 A1 | 11/2007 | Eliasen et al. |
| 2008/0033354 A1 | 2/2008 | Hartley et al. |
| 2008/0065011 A1 | 3/2008 | Marchand et al. |
| 2008/0103520 A1 | 5/2008 | Selkee |
| 2008/0125853 A1 | 5/2008 | Bailey et al. |
| 2008/0132989 A1* | 6/2008 | Snow ................ A61F 2/966 623/1.42 |
| 2008/0294230 A1 | 11/2008 | Parker |
| 2009/0024428 A1 | 1/2009 | Hudock, Jr. |
| 2009/0069889 A1 | 3/2009 | Suri et al. |
| 2009/0138079 A1 | 5/2009 | Tuval et al. |
| 2009/0157175 A1 | 6/2009 | Benichou |
| 2009/0192585 A1 | 7/2009 | Bloom et al. |
| 2009/0228093 A1 | 9/2009 | Taylor et al. |
| 2009/0276040 A1 | 11/2009 | Rowe et al. |
| 2009/0281619 A1 | 11/2009 | Le et al. |
| 2009/0299456 A1 | 12/2009 | Melsheimer |
| 2009/0319037 A1 | 12/2009 | Rowe et al. |
| 2010/0030318 A1 | 2/2010 | Berra |
| 2010/0036472 A1 | 2/2010 | Papp |
| 2010/0036473 A1 | 2/2010 | Roth |
| 2010/0049313 A1* | 2/2010 | Alon ................ A61F 2/2436 623/2.11 |
| 2010/0076402 A1 | 3/2010 | Mazzone et al. |
| 2010/0076541 A1 | 3/2010 | Kumoyama |
| 2010/0082089 A1* | 4/2010 | Quadri ................ A61F 2/95 623/1.11 |
| 2010/0094392 A1* | 4/2010 | Nguyen ............ A61M 25/0023 623/1.11 |
| 2010/0094394 A1 | 4/2010 | Beach et al. |
| 2010/0121425 A1 | 5/2010 | Shimada |
| 2010/0145431 A1 | 6/2010 | Wu et al. |
| 2010/0161036 A1 | 6/2010 | Pintor et al. |
| 2010/0174363 A1 | 7/2010 | Castro |
| 2010/0198347 A1 | 8/2010 | Zakay et al. |
| 2010/0274344 A1 | 10/2010 | Dusbabek et al. |
| 2010/0286768 A1* | 11/2010 | Alkhatib ............ A61F 2/2439 623/2.11 |
| 2010/0298931 A1* | 11/2010 | Quadri ................ A61F 2/243 623/2.11 |
| 2011/0015729 A1 | 1/2011 | Jimenez et al. |
| 2011/0054596 A1 | 3/2011 | Taylor |
| 2011/0137331 A1 | 6/2011 | Walsh et al. |
| 2011/0144690 A1* | 6/2011 | Bishop ................ A61F 2/2436 606/195 |
| 2011/0160846 A1 | 6/2011 | Bishop et al. |
| 2011/0251679 A1 | 10/2011 | Wiemeyer et al. |
| 2011/0264199 A1* | 10/2011 | Tran ................ A61F 2/2436 623/2.11 |
| 2012/0053681 A1* | 3/2012 | Alkhatib ................ A61F 2/243 623/2.11 |
| 2012/0123529 A1 | 5/2012 | Levi et al. |
| 2012/0239142 A1 | 9/2012 | Liu et al. |
| 2013/0030519 A1 | 1/2013 | Tran et al. |
| 2013/0211324 A1* | 8/2013 | Voss ................ A61B 17/3462 604/523 |
| 2013/0317598 A1 | 11/2013 | Rowe et al. |
| 2014/0236088 A1* | 8/2014 | Al-Rashdan ...... A61M 25/0606 604/164.03 |
| 2014/0296962 A1 | 10/2014 | Cartledge et al. |
| 2014/0343670 A1* | 11/2014 | Bakis ................ A61F 2/2436 623/2.11 |
| 2015/0018939 A1 | 1/2015 | Colson et al. |
| 2015/0289975 A1 | 10/2015 | Costello |
| 2016/0015512 A1* | 1/2016 | Zhang ................ A61F 2/2436 623/2.11 |
| 2016/0074067 A1* | 3/2016 | Furnish ................ A61B 17/34 606/108 |
| 2017/0014157 A1* | 1/2017 | Coyle ................ A61M 25/0023 |
| 2017/0065415 A1 | 3/2017 | Rupp et al. |
| 2017/0232236 A1* | 8/2017 | Al-Rashdan ........ A61M 25/002 604/96.01 |
| 2018/0153689 A1 | 6/2018 | Maimon et al. |
| 2018/0344456 A1 | 12/2018 | Barash et al. |
| 2018/0353312 A1* | 12/2018 | Wulfman .......... A61M 25/0662 |

FOREIGN PATENT DOCUMENTS

| | | |
|---|---|---|
| EP | 0592410 A1 | 4/1994 |
| EP | 0850607 A1 | 7/1998 |
| FR | 2815844 B1 | 1/2003 |
| WO | 9117720 A1 | 11/1991 |
| WO | 9829057 A1 | 7/1998 |
| WO | 9912483 A1 | 3/1999 |
| WO | 0149213 A2 | 7/2001 |
| WO | 0154625 A1 | 8/2001 |
| WO | 0176510 A2 | 10/2001 |
| WO | 0222054 A1 | 3/2002 |
| WO | 0236048 A1 | 5/2002 |
| WO | 0247575 A2 | 6/2002 |
| WO | 02060352 A1 | 8/2002 |
| WO | 03030776 A2 | 4/2003 |
| WO | 03047468 A1 | 6/2003 |
| WO | 2004019825 A1 | 3/2004 |
| WO | 2005084595 A1 | 9/2005 |
| WO | 2005102015 A2 | 11/2005 |
| WO | 2006032051 A2 | 3/2006 |
| WO | 2006111391 A1 | 10/2006 |
| WO | 2006138173 A2 | 12/2006 |
| WO | 2007047488 A2 | 4/2007 |
| WO | 2007067942 A1 | 6/2007 |
| WO | 2010121076 A2 | 10/2010 |

\* cited by examiner

IMPLANT DELIVERY CAPSULE

RELATED APPLICATIONS

This application is a continuation of U.S. application Ser. No. 16/448,418, filed Jun. 21, 2019, entitled "Implant Delivery Capsule," which is a continuation of U.S. application Ser. No. 15/331,564, filed Oct. 21, 2016, entitled "Implant-Delivery Capsule," which claims the benefit of U.S. Provisional Application No. 62/246,510, filed Oct. 26, 2015, entitled "Implant Delivery Capsule," where the contents and disclosure of applications referenced above are hereby incorporated by reference in their entirety.

FIELD

The present application concerns embodiments of a capsule and/or nosecone for use with an implant delivery catheter, and, in particular, a capsule and/or nosecone for reducing push forces associated with delivery of a prosthetic heart valve through a delivery sheath.

BACKGROUND

Endovascular delivery catheter assemblies are used to implant prosthetic devices, such as a prosthetic valve, at locations inside the body that are not readily accessible by surgery or where access without invasive surgery is desirable. For example, aortic, mitral, tricuspid, and/or pulmonary prosthetic valves can be delivered to a treatment site using minimally invasive surgical techniques.

An introducer sheath can be used to safely introduce a delivery apparatus into a patient's vasculature (e.g., the femoral artery). An introducer sheath generally has an elongated sleeve that is inserted into the vasculature and a housing that contains one or more sealing valves that allow a delivery apparatus to be placed in fluid communication with the vasculature with minimal blood loss. A conventional introducer sheath typically requires a tubular loader to be inserted through the seals in the housing to provide an unobstructed path through the housing for a valve to be mounted.

Conventional methods of accessing a vessel, such as a femoral artery, prior to introducing the delivery system include dilating the vessel using multiple dilators or sheaths that progressively increase in diameter. This repeated insertion and vessel dilation can increase the amount of time the procedure takes, as well as the risk of damage to the vessel.

One solution has been the development of radially expanding introducer sheaths. For example, U.S. Pat. No. 8,790,387, which is entitled EXPANDABLE SHEATH FOR INTRODUCING AN ENDOVASCULAR DELIVERY DEVICE INTO A BODY and is incorporated herein by reference, discloses a sheath with a split outer polymeric tubular layer and an inner polymeric layer, for example in FIGS. 27A and 28. A portion of the inner polymeric layer extends through a gap created by the cut and can be compressed between the portions of the outer polymeric tubular layer. Upon expansion of the sheath, portions of the outer polymeric tubular layer have separated from one another, and the inner polymeric layer is expanded from a folded configuration into a substantially cylindrical tube. Advantageously, the sheath disclosed in the '387 patent can temporarily expand for passage of implantable devices and then return to its folded configuration and associated starting diameter.

Expandable introducer sheaths, however, have some challenges. One of these challenges is that expandable sheaths can increase the amount of force needed to advance the delivery apparatus—such as a delivery catheter having mounted on its end a stent-mounted prosthetic heart valve—to the deployment site. Push forces also need to be mediated in conventional introducer sheaths.

As a result, there is a need to address the push forces required for delivery of implants through introducer sheaths.

SUMMARY

Disclosed herein is a delivery system for delivering a stent-mounted heart valve through an introducer sheath. The delivery system includes an elongate catheter supporting a capsule. The capsule contains the stent-mounted heart valve in the crimped condition. The delivery system also includes a nosecone with a tapered distal end and a proximal end. Surprisingly, the proximal end of the nosecone, despite having a larger profile than the capsule, reduces an average peak push force for advancing the delivery system through an introducer sheath.

In one embodiment, a delivery system for delivering a stent mounted heart valve through a sheath and into a patient vessel is provided. The delivery system includes an elongate catheter, a capsule and a nosecone. The elongate catheter has proximal and distal ends. The stent mounted heart valve is crimped at the distal end of the elongate catheter. The capsule extends around and encloses the crimped stent mounted heart valve. The capsule has a distal end with a capsule diameter. The nosecone includes a tapered distal end and a proximal end. The proximal end is engaged to the distal end of the capsule. Advantageously, the tapered distal end has a smooth continuous shape configured to progressively urge the sheath outward. Also, the proximal end has a nosecone maximum diameter greater than the capsule diameter so as to reduce an average peak push force resulting from advancement of the capsule through the sheath.

The delivery system can also include an inner catheter extending through the elongate catheter, capsule and stent mounted heart valve. The inner catheter, sometimes called a nosecone catheter, supports the nosecone on its distal end. Distal advancement of the inner catheter relative to the elongate catheter advances the stent mounted heart valve out of the capsule.

In another embodiment, the nosecone diameter is at least 1.002 times the capsule diameter. And, the upper tolerance limit of the peak push force is less than 40 Newtons and can even be less than 33 Newtons. The delivery system works particularly well when the sheath is an expandable sheath having a starting inner diameter less than the capsule diameter.

In another embodiment, the delivery system can include the expandable delivery sheath. The expandable delivery sheath includes a central lumen sized and configured to receive the elongate catheter, capsule and nosecone. The central lumen defines a starting inner diameter less than the capsule diameter. The sheath can be a 16 FR sheath and the elongate catheter can have a diameter from 23 mm to 29 mm.

The nosecone can, in one embodiment, include a progressive expansion portion, a rounded portion and an inflection point. The inflection point corresponds with or defines the nosecone maximum diameter. Also, the progressive expansion portion can be on the distal end of the nosecone, the rounded portion adjacent and proximal the progressive expansion portion and the inflection point is proximal the rounded portion. Even more proximal, the nosecone can include a proximal end proximal the inflection point and with a shrinking diameter relative to the maximum nosecone diameter.

Another embodiment includes, in addition to or as an alternative of the enlarged nosecone, one or more protrusions positioned on a distal region of the capsule and extending circumferentially around the capsule. The protrusion has a smooth continuous shape and is configured to urge the sheath away from the remainder of the capsule. The protrusion, for example, can be a ring extending circumferentially around an exterior surface of the capsule. Advantageously, the protrusion(s) reduce an average peak push force resulting from advancement of the capsule through the sheath. The protrusions can also have a greatest diameter that is at least 1.002 times the capsule diameter. Also, the upper tolerance limit of the peak push forces can be less than 40 Newtons, or even less than 33 Newtons.

Another embodiment includes, in addition to or as an alternative of the enlarged nosecone, a plurality of longitudinally extending ridges. The ridges protrude from the surface of the capsule. The ridges are configured to space the capsule surface from the sheath as it moves through the sheath. This reduces an average peak push force resulting from advancement of the capsule through the sheath. The ridges can also have a greatest diameter that is at least 1.002 times the capsule diameter. Also, the upper tolerance limit of the peak push forces can be less than 40 Newtons, or even 33 Newtons. In another aspect, the ridges include at least 6 ridges. The ridges can have a rectangular cross-sectional shape and extend around the circumference of the capsule so as to define alternating troughs and ridges.

Another embodiment includes a method of assembling a stent mounted heart valve onto a delivery system. The method includes providing a stent mounted heart valve supported by the delivery system. A nosecone is also provided. The nosecone has a tapered distal end and a proximal end. The tapered distal end has a smooth, continuous shape. The proximal end defines a nosecone maximum diameter. The method also includes advancing a distal open end of a capsule of the delivery system over the stent mounted heart valve until the distal open end of the capsule abuts the nosecone and the capsule surrounds the stent mounted heart valve. The capsule defines a diameter smaller than a maximum diameter of the nosecone.

The method can also include advancing the nosecone through an expandable delivery sheath by progressively urging the sheath outward with the smooth continuous shape of the nosecone to an inflection point defining the nosecone maximum diameter so as to reduce an average peak push force associated with advancing the stent mounted heart valve.

Another embodiment includes a method of delivering a stent mounted heart valve through a sheath and into a patient vessel. An expandable sheath is inserted into a vascular structure. A capsule carrying a stent mounted heart valve is loaded into a proximal end of the expandable sheath. The method also includes reducing an average peak push force resulting from advancement of the capsule through the sheath. Reduction is achieved by pushing the sheath away from the surface of the capsule using a friction-reducing feature.

DETAILED DESCRIPTION

The following description of certain examples of the inventive concepts should not be used to limit the scope of the claims. Other examples, features, aspects, embodiments, and advantages will become apparent to those skilled in the art from the following description. As will be realized, the device and/or methods are capable of other different and obvious aspects, all without departing from the spirit of the inventive concepts. Accordingly, the drawings and descriptions should be regarded as illustrative in nature and not restrictive.

For purposes of this description, certain aspects, advantages, and novel features of the embodiments of this disclosure are described herein. The described methods, systems, and apparatus should not be construed as limiting in any way. Instead, the present disclosure is directed toward all novel and nonobvious features and aspects of the various disclosed embodiments, alone and in various combinations and sub-combinations with one another. For example, the ridges, protrusions and/or nosecones with enlarged diameters described below could be combined in a single delivery system. The disclosed methods, systems, and apparatus are not limited to any specific aspect, feature, or combination thereof, nor do the disclosed methods, systems, and apparatus require that any one or more specific advantages be present or problems be solved.

Features, integers, characteristics, compounds, chemical moieties, or groups described in conjunction with a particular aspect, embodiment or example of the invention are to be understood to be applicable to any other aspect, embodiment or example described herein unless incompatible therewith. All of the features disclosed in this specification (including any accompanying claims, abstract, and drawings), and/or all of the steps of any method or process so disclosed, can be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract, and drawings), or to any novel one, or any novel combination, of the steps of any method or process so disclosed.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

As used in the specification and the appended claims, the singular forms "a," "an" and "the" include plural referents unless the context clearly dictates otherwise. Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal aspect. "Such as" is not used in a restrictive sense, but for explanatory purposes.

The terms "proximal" and "distal" as used herein refer to regions of the balloon, balloon catheter, or delivery catheter. "Proximal" means that region closest to handle of the device, while "distal" means that region farthest away from the handle of the device.

Disclosed herein is a delivery system for delivering a stent-mounted heart valve through an introducer sheath. The delivery system includes an elongate catheter supporting a capsule. The capsule contains the stent-mounted heart valve in the crimped condition. The delivery system also includes a nosecone with a tapered distal end and a proximal end. Surprisingly, the proximal end of the nosecone, despite having a larger profile than the capsule, reduces an average peak push force for advancing the delivery system through an introducer sheath.

Disclosed herein are tips and capsules for implant delivery catheters that are particularly suitable for delivery of implants in the form of implantable heart valves, such as self-expanding implantable heart valves, through expandable delivery sheaths. Self-expanding implantable heart valves are well-known and will not be described in detail here. An example of such an implantable heart valve is described in U.S. Pat. No. 8,652,202, which is incorporated herein by reference. Expandable delivery sheaths have elastic or sectioned portions that facilitate temporary profile expansion from the forces of the passing capsule and implant.

The capsules disclosed herein may also be used to deliver other types of implantable devices, such as self-expanding (or balloon expandable) implantable heart valves, stents or filters. The terms "implant" and "implantable" as used herein are broadly defined to mean anything—prosthetic or not—that is delivered to a site within a body. A diagnostic device, for example, may be an implantable. The term "implant" as used herein also does not need to be a permanent implant—for example devices used to deliver permanent implants are also implants temporarily. An implant could be any device delivered into the body for a procedure.

Figure 1:
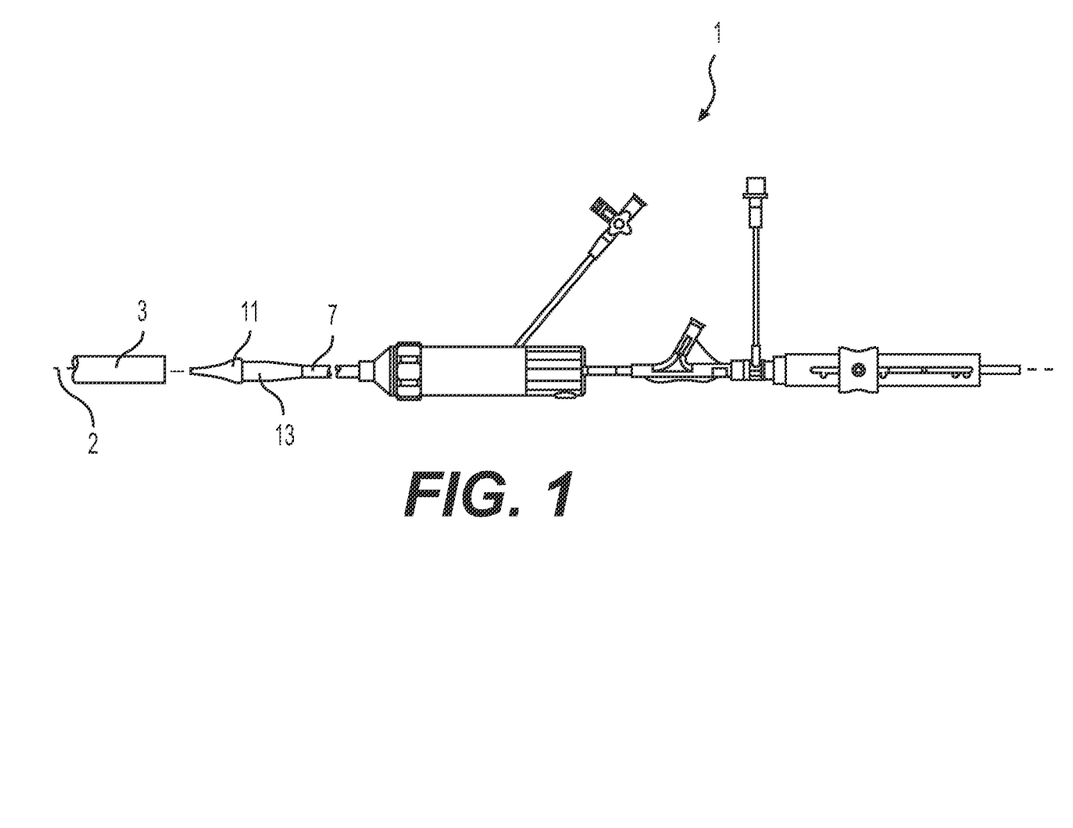
FIG. 1 is a side elevation view of a delivery catheter assembly being inserted into a delivery sheath of one embodiment of the present invention.

FIG. 1 illustrates a delivery catheter assembly 1 of one embodiment of the present invention including an elongate, expandable delivery sheath 3 with a lumen to guide passage of an implant delivery catheter supporting a prosthetic implant 5, such as a prosthetic heart valve. At a proximal end the sheath 3 includes a hemostasis valve that prevents leakage of pressurized blood. The delivery catheter assembly 1 can include a steerable guide catheter 7 (also referred to as a flex catheter). The delivery catheter assembly 1 can also include a capsule 13 which can have an enlarged diameter to hold the prosthetic implant 5. The capsule 13 can, for example, restrain a self-expanding implant to prevent premature expansion prior to reaching the procedure site. The delivery catheter assembly 1 also includes a contoured tip or nosecone 11 that can be joined with the capsule 13 to contain the prosthetic implant 5.

Figure 5A:
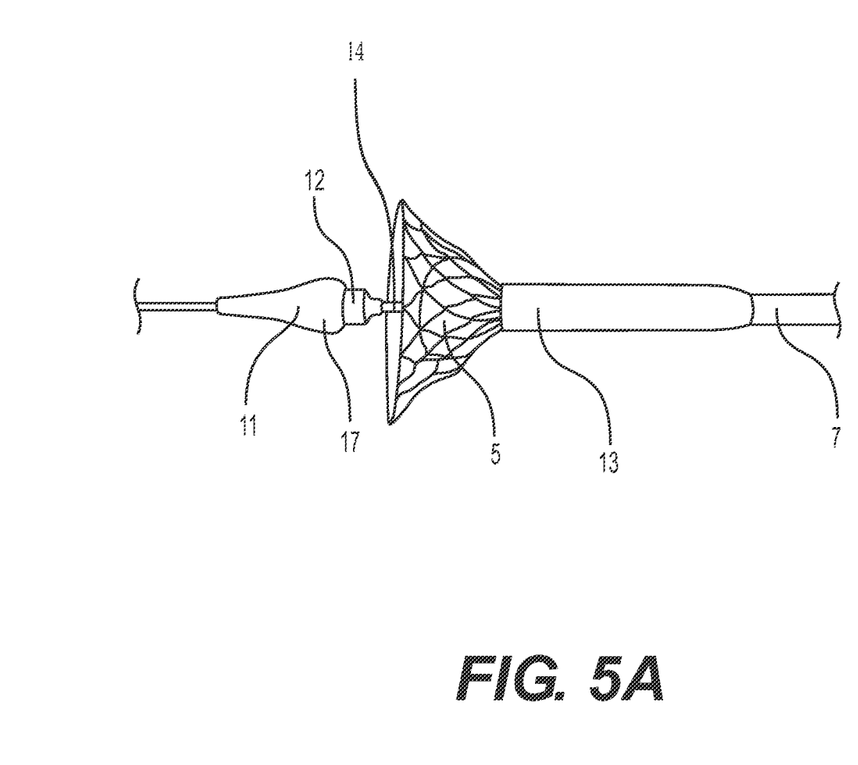
FIGS. 5A-5D depict a self-expanding implant as it is encased by withdrawal into a delivery capsule.

Generally, during use in one embodiment, the sheath 3 is passed through the skin of patient (usually over a guidewire) such that the distal end region of the sheath 3 is inserted into a vessel, such as a femoral artery, and then advanced to a procedure site—such as over the aortic arch to a native aortic heart valve. The nosecone 11 and capsule 13 are inserted through the hemostasis valve at the proximal end of the expandable sheath 3. The sheath 3 can be made at least partially of an elastic material and be expandable in the radial direction. Radial expansion facilitates the passage of the capsule 13 and nosecone 11. The steerable guide catheter 7 can be used to advance the nosecone 11 and capsule 13 through to and out of the end of the sheath 3. The nosecone 11 is separated from the distal end of the capsule 13, such as by advancement of an inner catheter 14 supporting the nosecone, as illustrated in FIG. 5A. The prosthetic implant 5 is advanced out of the capsule 13 along with the nosecone 11 and, in the embodiment having a self-expanding stent, expands in the native heart valve or other procedure site as it emerges from the capsule. The process could also reveal a balloon-expandable stent for subsequent balloon expansion.

Figure 2:
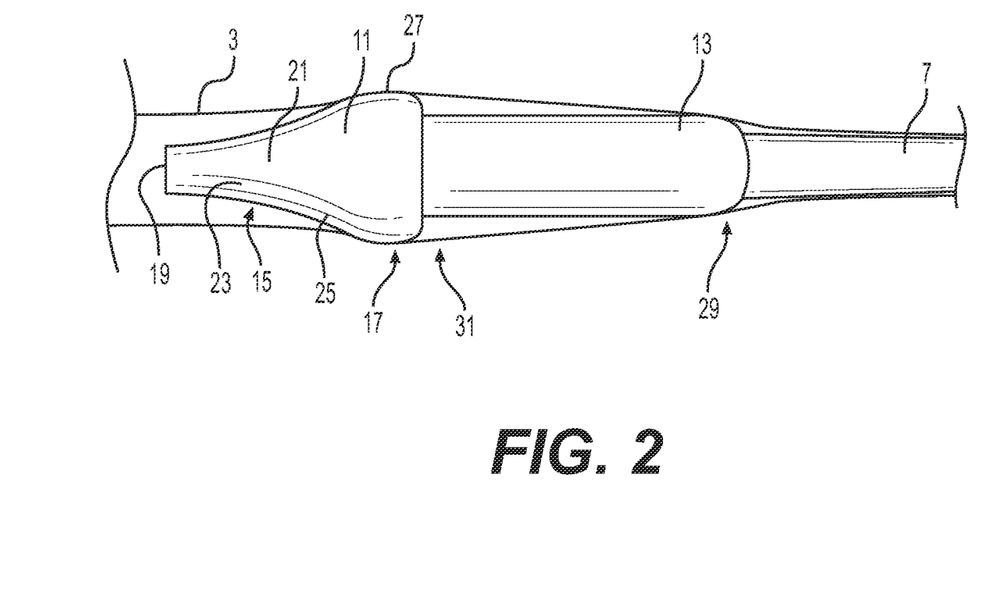
FIG. 2 is a side elevation view of an oversized nosecone and capsule of another embodiment of the present invention passing through an expandable delivery sheath.

As shown schematically in FIG. 2, in one embodiment, a distal end of the guide catheter 7 supports the capsule 13 and the nosecone 11 is mounted on the capsule 13. The external surfaces of the nosecone 11 and capsule 13 abut the adjacent, expanded wall surfaces of the delivery sheath 3.

The capsule 13, in one embodiment, has a cylindrical sleeve structure that defines a lumen configured to hold the prosthetic implant 5 in a crimped condition. The capsule 13 shown in FIG. 2 has a proximal end 29 and a distal end 31. The proximal end 29 of the capsule 13 can be coupled to the distal end of the guide catheter 7. In some embodiments, the proximal end 29 of the capsule 13 is an integral extension of a tubular sheath surrounding the outside of the distal end of the guide catheter 7. In other embodiments, the proximal end 29 of capsule 13 can be attached to the guide catheter 7, for example, by heat shrinking.

The distal end 31 of the capsule 13 has an opening extending distally that communicates with the lumen defined within the capsule. The lumen can be sized to hold the prosthetic implant 5 in its crimped, low profile state. The capsule 13 can be configured to also exert compression stress onto the prosthetic implant 5 to hold it in a crimped state. For example, the tubular wall structure of the capsule 13 can surround and have inner wall surfaces exerting restraining contact against outer surfaces of a self-expanding, nitinol frame stent of a prosthetic heart valve. The distal end 31 of the capsule 13 in the illustrated embodiment has a circular free edge (not shown) that can be mated with a correspondingly sized and shaped opening (not shown) in the proximal-facing surface of the nosecone. Additional details of an exemplary delivery capsule can be found in commonly assigned U.S. Patent Publication No. 2014/0343670, which is hereby incorporated herein by reference.

As shown in FIG. 2, in one embodiment, the nosecone 11 includes a tapered distal end 15 and a proximal end 17. The distal end 15 of the nosecone 11 includes a distal facing surface 19 and a contoured surface 21. The distal facing surface 19 can be a flat, circular surface that has a smaller profile or diameter than the remainder of the body of the nosecone 11. The distal facing surface 19 also has about the same, or smaller, diameter than the adjacent guide catheter 7. Generally, the distal end facing surface 19 is sized to fit within the unexpanded diameter of the sheath 3 and has an atraumatic (such as flat) shape for safety reasons. Other atraumatic shapes can be rounded or hemispherical shapes. Also, other non-circular shapes can be used for the distal facing surface 19.

The contoured surface 21 of the nosecone 11 is, in one embodiment, axisymmetric and starts with the small diameter of the distal facing surface 19 and expands in diameter moving proximally (towards the cardiologist holding the handle) until reaching the proximal end 17. The contoured surface 21 can be broken down into a progressive expansion portion 23, a rounded portion 25 and an inflection point 27. The progressive expansion potion 23 expands smoothly at a rate increasing with proximal progression before splining into the rounded portion 25. The rounded portion 25 is more bulbous with a slowed expansion of diameter in the proximal direction until the inflection point 27, at which point the diameter begins to decrease moving proximally. Restated, the inflection point 27 defines the largest diameter (or nosecone diameter) where the expansion in diameter of the contoured surface 21 stops and then the proximal end 17 begins with a shrinking diameter. Thus, at the inflection point 27 the proximal-most boundary of the distal end 15 (and of the contoured surface 21) and the distal-most boundary of the proximal end 17 share the same largest diameter.

As shown in FIG. 2, the distal end 31 of the capsule 13 has a smaller diameter than the maximum diameter of the proximal end 17 of the nosecone 11, thus the nosecone is oversized relative to the capsule. Surprisingly, the inventors have determined that this oversizing actually reduces the forces needed to advance the capsule 13 through the sheath 3 to its deployment location. Without being wed to theory, the inventors believe that the oversized diameter of the nosecone 11 pushes the expandable sheath 3 wall away from the capsule 13 at an angle. Pushing the expandable sheath away from the capsule reduces the contact area between the two and thus reduces the friction of the sheath 3 (which includes an elastic component compressing it inwards) against the advancing capsule 13. Also, the oversized nosecone 11 can act as a dilator making the rest of the sheath 3 more compliant for the remainder of the delivery catheter assembly 1.

Notably, the term "diameter" as used herein is not limited to circular cross-sections. Instead, diameter refers to a width through a centroid of the cross-section of the shape, such as a cross-section of the nosecone 11 taken perpendicular to the long-axis of the catheter assembly 1. Although circular cross-sections are shown for the nosecone 11 and/or the capsule 13, they can have other shapes, such as ovals, rounded rectangles and other shapes, including irregular shapes. The maximum diameter of such cross-section is simply the largest diameter seen by the expandable delivery sheath 3 as the nosecone 11 and capsule 13 are advanced therethrough. Generally, then the concept of enlarged profiles for the nosecone 11 (and the capsule 13) are realized when some diameter is larger than the base capsule 13 itself needed to hold and deliver the implant 5. Thus, the elliptical cross-section can have a major axis that exceeds the capsule 13 and a minor axis that matches the capsule 13 and still serves to open up the sheath 3 and reduce advancement forces for the trailing capsule 13.

In some embodiments, the capsule 13 can be made of or coated by polyether ether ketone (PEEK). PEEK is advantageously a lubricious polymer, but other lubricious materials could also be used for—or coated on—the surfaces of the nosecone 11.

Push forces were calculated for various nosecone designs. The sheath 3 used in testing was an expandable E-SHEATH from Edwards Lifesciences, Inc. (U.S. Pat. No. 8,790,387, which is hereby incorporated by reference in its entirety). The sheath 3 was extended through a model of an aorta in a water bath at a temperature of 37 degrees C. A 0.035" extra-stiff guidewire was inserted through the entire length of the aortic model. The sheath 3 with the introducer was inserted into the aortic model over the guidewire. The water level was verified to be up to the hub of the sheath 3. The hub of the sheath 3 was secured to a force gauge plate using a zip tie.

The proximal end of the guidewire was inserted through the catheter nosecone and pushed through the catheter until being exposed from the back end of the catheter. The nosecone tip 15 was then advanced over the guidewire until positioned at the proximal side of the first seal in the introducer housing. The force gauge was zeroed and a timer started. Then, the guidewire was pinned and the nosecone further advanced over the guidewire and through the seal of the sheath 3. The nosecone and capsule 11, 13 continued to be advanced through the remainder of the sheath 3 until exiting the tip of the sheath. The insertion time from start to finish was within 20-30 seconds. The forces, including peak push force, and insertion time were measured. Push forces were determined at each 2 cm of advancement through the delivery sheath 3.

Table 1 below shows the results of the peak push force testing when the nosecone 11 was oversized by various amounts. Typically, an increase in the diameter of the delivery capsule 13 yields higher peak push forces due to increased frictional forces between the capsule 13 and the sheath 3. However, providing a nosecone 11 with a greater diameter than the capsule 13 diminished the peak push forces, in some cases down to the mid 20 N range. The capsule delivery cylinder outside diameter is shown in the first column and the oversizing of the nosecone 11 in thousands of an inch is shown in the second column. The values in the oversizing column represent the difference between the widest diameter of the nosecone 11 and the outer diameter of the capsule delivery cylinder. The "N" column shows the number of tests. The term UTL designates the statistical upper tolerance limit of the data acquired from the peak push force testing.

TABLE 1

Push Force Summary Through 14 Fr E-Sheath-PEEK Delivery Cylinder (Capsule)

| Delivery Cylinder OD (in) | Nose Cone Over Sizing (in) | N | Avg Peak Push Force (N) | UTL of Peak Push Force (N) | Nosecone/ capsule diameter ratio |
|---|---|---|---|---|---|
| 0.253 | 0.010 | 2 | 20.5 | * | 1.040 |
| 0.253 | 0.001 | 2 | 32.5 | * | 1.004 |
| 0.251 | 0.001 | 2 | 29.5 | * | 1.004 |
| 0.269 | 0.006 | 15 | 26.4 | 32.6 | 1.022 |
| 0.244 | 0.001 | 15 | 25.3 | 32.6 | 1.004 |

Generally, the desired upper tolerance limit for peak force is about 45 N. To meet this criteria, an average peak force of 25-30 N is targeted. Experimentation showed that the nosecone diameter being at least 1.002 times the capsule diameter, for example, from 1.002 to 1.045 times the capsule diameter, gave a peak push force upper tolerance limit of less than 40 N, and in particular less than 33 N. Notably the higher forces were present in the smaller diameter oversizing.

The sheath 3 used to attain the testing values shown in Table 1 had a standard 14 French diameter. However, the size of the nosecone 11 and capsule 13 can be adapted to other sheath sizes to attain similar values for peak push forces. For example, other verification tests were run using 16 French sheaths and CENTERA Model 9550C catheters with sizes of 23 mm, 26 mm and 29 mm. The average peak push force and the upper tolerance limit of the push force were under the 40 N threshold during these other verification tests.

Beyond push force reduction, the oversized nosecone 11 has the advantage of being easy to manufacture (by molding). Also, the oversized nosecone 11 works well with a capsule 13—especially a capsule having its distal end 31 with a thinned out wall. The thinned out wall promotes flaring for easier withdrawal and recapture of the prosthetic implant 5 within the capsule 13. And, the oversized nosecone 11, because of its larger diameter, can still mate with the flared-out distal end 31 of the capsule 13.

Figure 3:
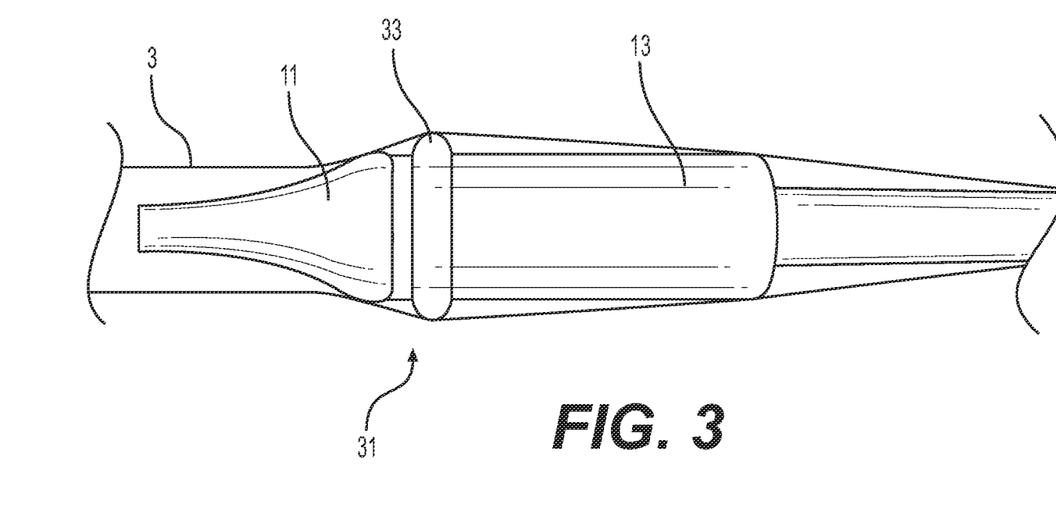
FIG. 3 is a side elevation view of a nosecone and capsule with a friction reducing protrusion of another embodiment of the present invention passing through an expandable delivery sheath.

FIG. 3 shows an example capsule 13 of another embodiment including one or more bumps or other protrusions 33 positioned on the distal end 31 of the capsule. For example, the protrusion 33 can be an annular protrusion extending circumferentially around (in a ring) the entirety of the distal end 31 of the capsule 13. Like the nosecone 11, the protrusion 33 can have a smooth, continuous shape. The protrusion 33's configuration urges the sheath 3 away from the exterior of the capsule 13. The protrusions 33 thus can also reduce the average peak push force resulting from advancement of the capsule 13 through the sheath 3.

The protrusions 33 can also include one or more rounded bumps, e.g., hemispherical-shaped protrusions, arranged in a spaced array around the distal end 31 of the capsule 13. The protrusions 33 could also be combined with an oversized nosecone 11.

Figure 4A:
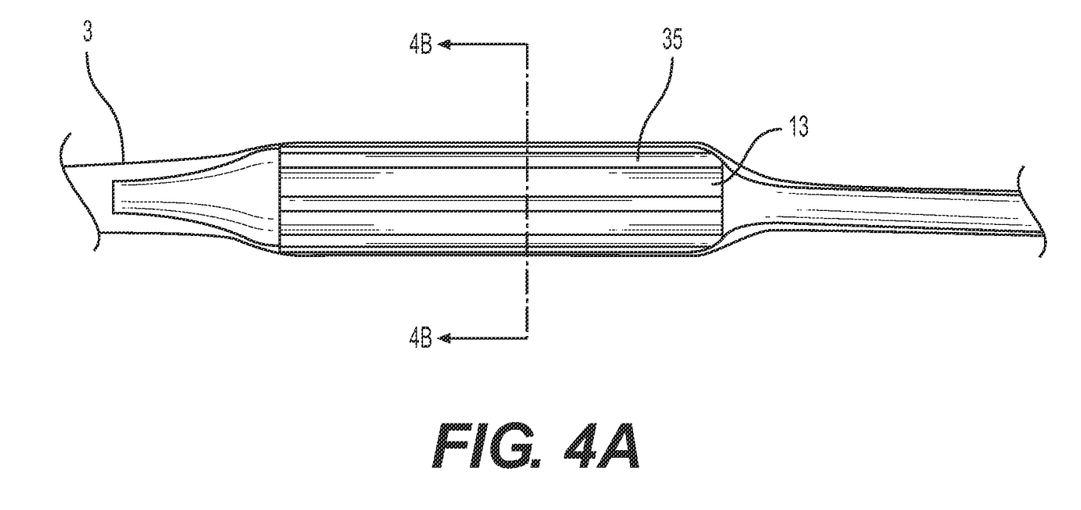
FIG. 4A is a side elevation view of a capsule with longitudinal ridges of another embodiment of the present invention passing through an expandable sheath.
Figure 4B:
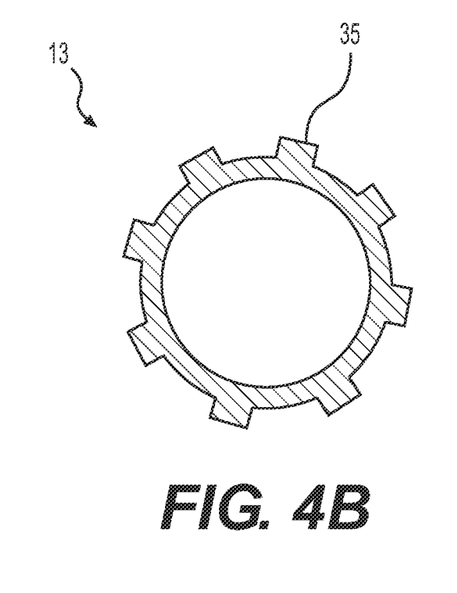
FIG. 4B is cross-sectional view of the capsule of FIG. 4A.

FIGS. 4A and 4B show another example capsule 13 including a plurality of ridges 35 extending longitudinally along the outside surface of the capsule 13. The ridges 35 are sized and spaced so as to space the inside of the sheath 3 away from the capsule 13 as it advances along the inside of the sheath 3. The ridges 35 are shown in FIG. 4A as having parallel edges extending longitudinally in the direction of the axis of the delivery catheter assembly 1 and as having rectangular cross-sectional shapes in FIG. 4B. The ridges 35 extend around the capsule in a spaced arrangement and are preferably 6 to 16 in number.

As illustrated in FIG. 4B, the capsule 13 can include a plurality of ridges 35 having the same height, the height of a ridge 35 measured between the outer surface of the capsule and outer surface of the ridge 35. It is contemplated that the capsule 13 can include a plurality of ridges 35 having different heights. As shown in FIG. 4B, an outer diameter of the capsule 13 defined the ridges 35 can be determined by the distance between the outer surfaces of two opposing ridges 35. The outer diameter can also be determined by taking an average height of the ridges and adding it to the diameter of the capsule 13.

Other cross-sectional shapes for ridges 35 can also be employed, such as rounded, square, irregular or semi-circular shapes. Advantageously, by adding ridges 35 along the length of the capsule 13—which defines the largest diameter of the delivery catheter assembly 1—the frictional force between the capsule 13 and the inside surface of the sheath 3 may be reduced. This is believed to be a result of changing the contact area between the capsule 13 and the inside diameter of the sheath 3. It is also contemplated that the spacing between the ridges 35 could vary to reduce contact area between the capsule 13 and the sheath 3.

Figure 5B:
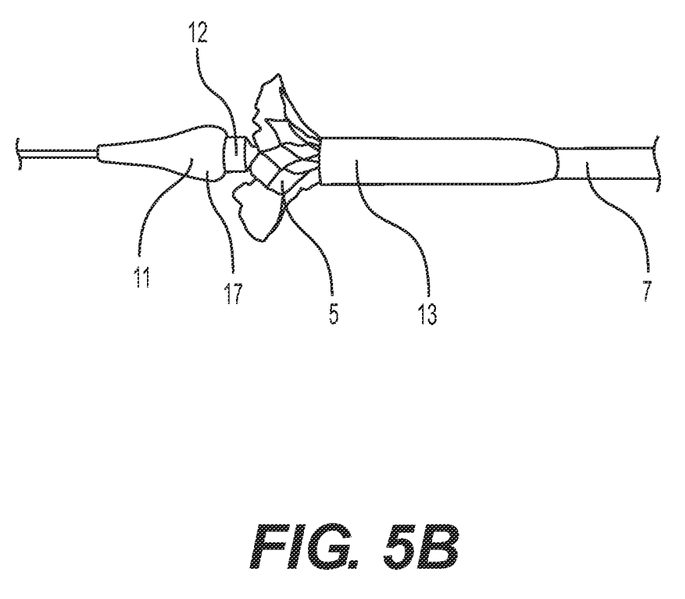
Figure 5C:
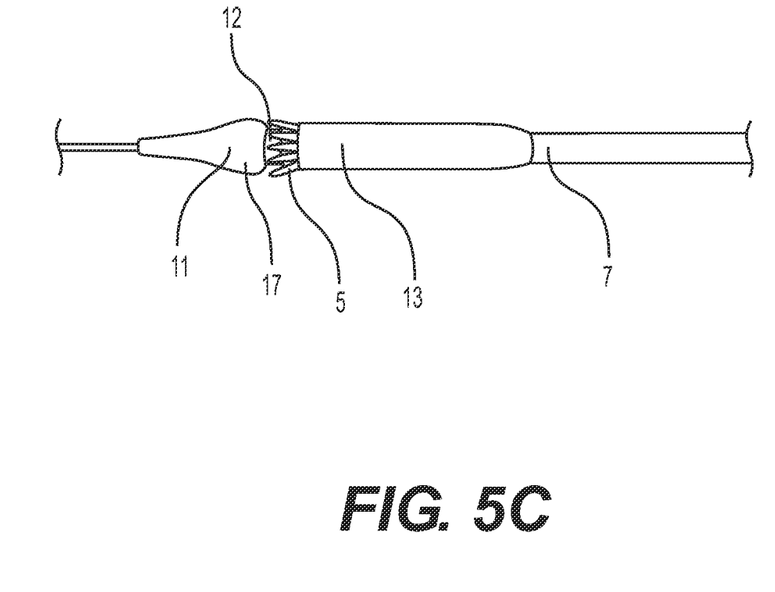
Figure 5D:
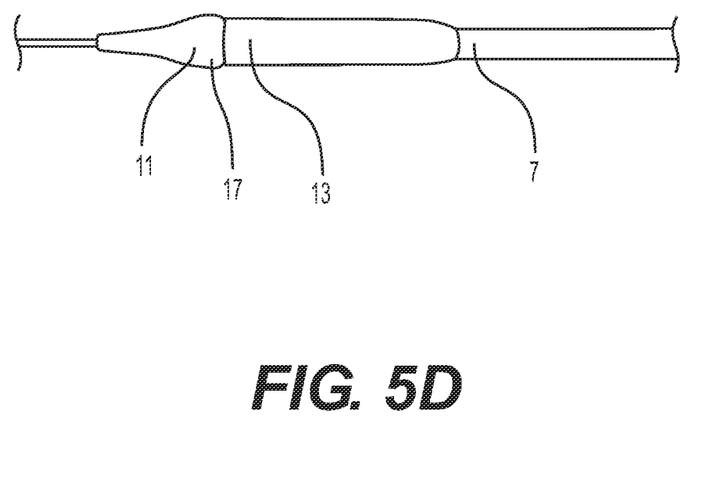

FIGS. 5A-D show a method of encasing a prosthetic implant 5 such as a self-expanding heart valve 5 in a capsule 13 to prepare it for delivery (or to retrieve it when needing to be repositioned within the patient). In this embodiment, the nosecone 11 includes a neck 12 positioned proximal the proximal end 17. The neck has a stepped down diameter and a cylindrical shape. In the embodiment of FIG. 5A, the self-expanding heart valve 5 can be partially encased in the capsule 13 with its proximal end coupled to the delivery system, such as the nosecone catheter. The capsule 13 is then slid distally over the remainder of the self-expanding heart valve 5 so that less of it is visible, as illustrated in FIG. 5B. As shown in FIG. 5C, the capsule 13 continues sliding distally until only the distal end of the self-expanding heart valve 5 is visible, and it is in close proximity with proximal end 17 of the nosecone 11. Also, at this stage, the distal stent structure of the implant 5 overlaps onto and can be supported by the neck 12. FIG. 5D illustrates the capsule 13 slid completely over the self-expanding heart valve 5 such that the distal end of the self-expanding heart valve 5 can be sandwiched between the neck 12 of the nosecone 11 and the distal end 31 of the capsule 13. Also, in this position the distal end of the capsule 13 abuts the proximal end 17 of the nosecone 11 where its diameter steps up from the neck 12.

During a procedure, the process of FIGS. 5A-D can be reversed and continued for complete withdrawal of the capsule 13 from coverage of the implant 5. Then the stent mounted heart valve 5 can be released (if it is self-expanding and anchored, for example) or expanded via balloon or other device. Also, if the implant is needing to be retrieved for repositioning or removal, the procedure of FIGS. 5A-D can be repeated to retract the implant back into the capsule 13.

In view of the many possible embodiments to which the principles of the disclosed catheter assembly can be applied, it should be recognized that the illustrated embodiments are only preferred examples and should not be taken as limiting in scope. Rather, the scope of the disclosure is defined by the following claims. We therefore claim as our invention all that comes within the scope and spirit of these claims.

What is claimed is:

1. A method of assembling a delivery system for a stent mounted heart valve, the method comprising:
   supporting the stent mounted heart valve on a distal end of an elongate catheter;
   extending an inner catheter through the elongate catheter and extending a distal end of the inner catheter out of the distal end of the elongate catheter;
   coupling a proximal end of a nosecone to the distal end of the inner catheter, the nosecone having a tapered distal end with a smooth continuous shape and the proximal end of the nosecone defining a nosecone maximum diameter; and
   extending a capsule proximally from a proximal end of the nosecone over the stent mounted heart valve and surrounding the stent mounted heart valve with the capsule and defining a capsule diameter smaller than the nosecone maximum diameter, the capsule including a protrusion extending from an outer surface of the capsule a position proximal to a distal end of the capsule and extending circumferentially around at least a portion of the capsule diameter.

2. The method of claim 1, further comprising sizing and shaping the smooth continuous shape of the tapered distal end of the nosecone to progressively enlarge a central lumen of an expandable delivery sheath outward from a starting inner diameter less than the capsule diameter and reduce an average peak push force for the elongate catheter.

3. The method of claim 2, further comprising forming a progressive expansion portion, a rounded portion and an inflection point on the nosecone.

4. The method of claim 3, wherein forming the inflection point includes forming the inflection point as the nosecone maximum diameter.

5. The method of claim 4, wherein forming the progressive expansion portion includes forming the progressive expansion portion on a distalmost end of the nosecone, forming the rounded portion includes forming the rounded portion adjacent and proximal to the progressive expansion portion and forming the inflection point includes forming the inflection point proximal the rounded portion.

6. The method of claim 5, further comprising forming the proximal end of the nosecone proximal to the inflection point with a shrinking diameter relative to the maximum diameter.

7. The method of claim 2, further comprising forming the nosecone maximum diameter to be at least 1.002 times the capsule diameter.

8. The method of claim 7, wherein sizing and shaping the smooth continuous shape includes limiting a peak push force to less than 40 newtons.

9. The method of claim 7, wherein sizing and shaping the smooth continuous shape includes limiting a peak push force to less than 33 newtons.

10. The method of claim 2, further comprising forming the nosecone maximum diameter to be 1.002 times to 1.045 times the capsule diameter.

11. A method for delivering a stent mounted heart valve into a patient vessel, the method comprising:
    inserting an expandable delivery sheath through the patient vessel, the delivery sheath having a central lumen;
    advancing a catheter assembly, including a nosecone having a nosecone maximum diameter and a capsule surrounding the stent mounted heart valve and having a capsule diameter smaller than the nosecone maximum diameter, through the central lumen of the delivery sheath; and
    progressively enlarging the central lumen of the delivery sheath, with a smooth continuous shape of a tapered distal end of the nosecone, from a starting inner diameter less than the capsule diameter to an enlarged inner diameter larger than the capsule diameter and reducing an average peak push force for the catheter assembly.

12. The method of claim 11, wherein advancing the catheter assembly includes advancing the smooth continuous shape of the nosecone through the central lumen of the expandable delivery sheath to an inflection point defining the nosecone maximum diameter.

13. The method of claim 12, further comprising advancing an inner catheter of the catheter assembly, the inner catheter supporting the nosecone and the stent mounted heart valve, relative to an elongate catheter of the catheter assembly, the elongate catheter supporting the capsule, to separate a proximal end of the nosecone from a distal open end of the capsule.

14. The method of claim 13, wherein further advancing the inner catheter relative to the elongate catheter to advance the stent mounted heart valve out of the capsule.

15. The method of claim 11, wherein advancing the catheter assembly further comprises pushing the catheter assembly with a force less than 40 newtons.

16. The method of claim 11, wherein advancing the catheter assembly further comprises pushing the catheter assembly with a force less than 33 newtons.

17. The method of claim 11, wherein the nosecone maximum diameter is 1.002 times to 1.045 times the capsule diameter.

18. The method of claim 11, further comprising enlarging the central lumen of the delivery sheath with a plurality of longitudinally extending ridges protruding from an outermost surface of the capsule.

19. The method of claim 11, wherein progressively enlarging the central lumen includes progressively enlarging the central lumen with a progressive expansion portion on a distalmost end of the nosecone, a rounded portion adjacent and proximal to the expansion portion and an inflection point proximal the rounded portion and defining the nosecone maximum diameter.

20. The method of claim 11, further comprising reducing an expansion force on the delivery sheath with a shrinking diameter of a portion of the nosecone proximal the inflection point.

* * * * *